United States Patent [19]

Hochberg

[11] 3,991,100

[45] Nov. 9, 1976

[54] PROCESS FOR MAKING ESTERS OF DIBASIC ACIDS FROM ACID BY-PRODUCTS

[75] Inventor: Seymore Hochberg, Wynnewood, Pa.

[73] Assignee: E. I. Du Pont de Nemours and Company, Wilmington, Del.

[22] Filed: Jan. 20, 1975

[21] Appl. No.: 542,565

Related U.S. Application Data

[63] Continuation-in-part of Ser. No. 430,049, Jan. 2, 1974, abandoned, which is a continuation-in-part of Ser. No. 113,058, Feb. 5, 1971, abandoned.

[52] U.S. Cl. .......................... 260/485 R; 260/485 S
[51] Int. Cl.² .................. C07C 69/34; C07C 69/44
[58] Field of Search .................... 260/485 R, 485 S

[56] References Cited

UNITED STATES PATENTS

| | | | |
|---|---|---|---|
| 2,560,156 | 7/1951 | Cavanaugh et al. | 260/485 S |
| 2,805,246 | 9/1957 | Bourguignon et al. | 260/475 B |
| 2,824,123 | 2/1958 | Kuceski | 260/485 S |
| 3,717,672 | 2/1973 | McGee | 260/485 S |

Primary Examiner—Jane S. Myers

[57] ABSTRACT

A process for making alkyl esters of $C_4$ to $C_{12}$ dibasic acids such as glutaric, adipic and dodecanedioic acid from the mother liquors of an acid crystallization process is provided.

7 Claims, No Drawings

PROCESS FOR MAKING ESTERS OF DIBASIC ACIDS FROM ACID BY-PRODUCTS

CROSS REFERENCE TO RELATED APPLICATIONS

This application is a continuation-in-part of copending application Ser. No. 430,049, filed Jan. 2, 1974, now abandoned, which in turn is a continuation-in-part of application Ser. No. 113,058, filed Feb. 5, 1971, now abandoned.

BACKGROUND OF THE INVENTION

Dicarboxylic acids, e.g. adipic and dodecanedioic, are produced by the oxidation of cyclic hydrocarbons, e.g. ketones and alcohols and the further oxidation of these by nitric acid to the dicarboxylic acids. These processes produce dibasic acid waste products which become part of waste streams that must be discarded. Disposal of these waste streams has been expensive and detrimental to the ecology campaign which is of immediate interest since these by-products are currently burned or buried.

Dodecanedioic acid, used in some nylon manufacture, is made by nitric acid oxidation of $C_{12}$ cyclic hydrocarbon. This process also produces $C_4$ to $C_{12}$ dibasic acid waste products that also must be discarded.

Various techniques are available for separation, recovery and purification of the dibasic acids by crystallization. The preparation of esters from the purified acids is a well-known process. The preparation of esters from acids not crystallized by reaction with alcohols commonly produces yellowish esters, whose color is accentuated by alkaline conditions and by heating, particularly under the alkaline conditions often used for transesterifications.

SUMMARY OF THE INVENTION

This invention relates to a process of making alkyl esters of various dibasic acids which are colorless and remain light in spite of heating and alkaline conditions. Typical sources of these dibasic acids are waste streams from the manufacture of adipic acid and dodecanedioic acid via nitric acid oxidation.

This process comprises esterifying the dibasic acid in the presence of an acid catalyst and alcohol and removing substantially all of the water formed. This is followed by distilling off the alkyl esters which are formed in the esterification step. The distillation is carried out under basic conditions.

DESCRIPTION OF THE INVENTION

This invention particularly relates to a process of producing alkyl esters of dibasic acids containing 4 through 12 carbons. These dibasic acids are contained in waste streams produced in the synthesis of adipic acid or dodecanedioic acid. The synthesis of adipic acid is carried out by air oxidation of cyclohexane to cyclohexanone and cyclohexanol. This is followed by oxidation of the cyclohexanone and cyclohexanol by nitric acid to adipic acid. The adipic acid is crystallized and filtered from a mother liquor containing by-products of the oxidation and incidental impurities. The stream therefore contains mainly adipic, glutaric and succinic acids and small amounts of monobasic acids, copper, vanadium, ammonia, iron, sodium and unidentified colored organic impurities.

Another source of acids for treatment according to the process of the present invention is the high boiling residue from the distillation of the ketone and alcohol oxidate. In a preferred embodiment this residue is contacted with nitric acid and at elevated temperature and the resultant product is treated according to the present process.

The initial step of this invention consists of heating the mother liquor or the oxidized residue waste stream to about 130°–150° C., preferably to about 140° C. at about 100 to 760 mm. Hg pressure. This removes water, oxides of nitrogen and nitric acid. This step can be maintained until no additional water, oxides of nitrogen or nitric acid is being evolved. Not all of the water or nitric acid needs to be removed at this time, although it is preferable to remove it prior to the addition of methanol. This dehydration can be performed either in a batch process or continuously. The presence of copper during the dehydration may have an effect on the quality of the refined product. Amounts of copper in the range of 1000–3000 ppm appear in some cases to improve the color of the final ester product.

The second step of this process consists of introducing an alcohol of 1–4 carbons such as methanol, ethanol, propanol, butanol, isobutanol and isopropanol with methanol preferred, into the mother liquor. An acid catalyst such as $H_2SO_4$ is also used in about 0.5 to 1.0% by weight of acids in excess of the amount required to form salts with the inorganic impurities present. A similar amount of an acid ion exchange resin or $H_3PO_4$ can be effectively used in place of $H_2SO_4$. An esterification reaction is then conveniently carried out at about 120°–160° C. The acid catalyst shortens reaction time. The acidity of mother liquor can be monitored via a glass electrode, e.g. to a pH reading of below 0 on the meter after calibration in an aqueous solution in the usual fashion.

During the second step of the reaction an alcohol is reacted with the acids, and water is formed. The reaction reaches an equilibrium. Esterification is brought nearer to completion by reduction of the concentration of water. The water is usually removed by distillation, during which a mixture of water and alcohol is evaporated from the reaction mixture. The evaporated alcohol may be separated from the water by fractional distillation and returned to the reaction mixture. An alternate procedure is to add dry alcohol continuously to a heated vessel and to remove a mixture of water and alcohol vapors, until the distillate is approximately dry.

If the reaction is done by a batch process, the first distillates will be rich in water; the last distillates will be low in water content and will also contain small amounts of the esters. All the distillates can be separated by fractional distillation into pure water, pure alcohol and a mixture of diester and monoester. Of these only the pure water need be discarded, the remainder returned to the reaction vessel or to a subsequent batch. As an alternative, the distillates relatively low in water content and high in alcohol content can be used instead of dry alcohol for the first part of a new batch.

It is preferred, although optional, that either the oxidized residue, the mother liquor or the crude esterified product be further heated to reduce the volatility of heat-discoloring materials present. Heating, which gives further improvement in color, is preferably conducted at a temperature up to 270° C. for a time sufficient to render nonvolatile any heat-discoloring materials present. Temperatures above 270° C. and elevated pressure can be employed. The optimum temperature and time varies depending upon the composition of the waste stream and the final product color desired. Usually heating to about 220° C. for about three hours is sufficient.

At the end of the second step or the above-described heat treatment containing copper and vanadium salts can form. These salts can be filtered off and recovered usefully but the filtration is not necessary to the preparation of useful esters.

The third step of this process is most critical to the development of esters of low color and acidity. For optimal yield the acid number of the crude dimethyl esters should be about 20 or below, preferably below 10. While an excess of a base selected from the group consisting of $Na_2CO_3$, $NaHCO_3$, $K_2CO_3$, CaO and Ca(OH)$_2$ is used, the optimum quantity in excess will vary from base to base. For example, with $Na_2CO_3$, about 0.7 to 0.9 mole $NaCO_3$ per one equivalent of titratable acidity, preferably about 0.85 mole, is added to the crude esters at 100°–120° C. with the evolution of carbon dioxide and ammonia gases. This usually amounts to about 1 to 4% by weight of $Na_2CO_3$ based on the weight of the crude ester product. After removing volatile nitrogen containing compounds, e.g. $NH_3$, a small forecut (about 5%) is distilled at 130° C. (1 atm) in order to remove the esters of monobasic acids, water and methanol. Subsequent distillation of this forecut can be performed to recover the methyl esters of the dibasic acids for recycling.

Continued distillation of the esters at 115° C./25 mm. Hg gives refined ester having low acidity and low alkaline color (Gardner). The alkaline color is developed by treating the esters with tetrabutyl ammonium hydroxide at 25° C. and measuring the color intensity on a Gardner scale. The acidity of these esters is determined by titration. When the acidity of refined ester increases, additional sodium carbonate (10%) can be added, and the distillation process can then be continued. If the quantity of sodium carbonate is too great, however, yield loss through the saponification of the esters can occur. Ester having higher acidity and color results if too little carbonate is used.

Other factors besides the quantity of $Na_2CO_3$ are important in the purification of these esters. Prolonged exposure of these esters to sodium carbonate can give esters of poorer quality. Thus, the time of contact between the ester and $Na_2CO_3$ should be minimal for best results.

Below 100° C. there is poor removal of acidity from these esters by $Na_2CO_3$. At 150° C. the formation of acidic materials is greater than can be effectively removed. Consequently, the best results are obtained at 115°–120° C., the temperature at which the distillation is performed.

The effect of water is an additional factor in the treatment of these esters. Although the removal of the acidic materials occurs readily with water in excess, extensive hydrolysis of these esters occurs during the distillation. The use of smaller quantities of water is thus beneficial since these hydrolysis reactions are minimized.

Other bases besides $Na_2CO_3$ will produce low color and low acidity in these esters. Lime (Ca(OH)$_2$ or CaO is added to an excess as judged from alkalinity of vapors (traces of $NH_3$) and a glass electrode pH reading of 7 or more. The mother liquor is then distilled while alkaline conditions continuously prevail in the distillation pot. If ammonia is not present in the system it preferably should be added in an amount of up to 0.05% by weight of the base to increase the rapid development of a basic system. A predistillation time of about 30 minutes at 100° C. is required in order to remove methyl sulfate and $NH_3$ fractions. Following the predistillation, the distillate should contain esters of monobasic acids in trace amounts, the methyl esters of the various dibasic acids, and trace amounts of water and methanol which can be easily separated. A small forecut, about 5%, will contain substantially all the alcohol, esters of monobasic acids and water.

If step 3 is carried out improperly, two sources of difficulty are apt to arise. Alkyl esters of the catalyst acids, e.g. methyl sulfate, will be distilled with the methyl esters of interest in small but damaging quantities—about 0.01% by weight. Also small quantities of material (presumably nitro phenols such as picric acid and other reducible nitrogen compounds) which turn yellow in aqueous alkali and which darken on heating, particularly in the presence of metal oxides or salts, are liberated. In order to preclude these difficulties from occurring, the aforementioned alkaline conditions must be maintained in the mother liquor long enough to decompose any methyl sulfate and to distill the esters. A way to accomplish this result is to use a metallic hydroxide like slaked lime together with a small amount of ammonia to improve diffusion of acid and base. The ammonia may be derived from compounds present in traces in the mother liquor as salts, amides, or nitriles or it may be introduced as a salt, gas or aqueous solution. In any case, quantities of ammonia of the order of 0.05% are usually sufficient. In step 3, after addition of the lime and neutralization, the product may be filtered thereby removing any color formers and making further control of alkalinity during distillation unnecessary.

An optional step of this process is to pass the distillate of step 3 over an acid ion exchange resin to remove traces of ammonia.

DESCRIPTION OF PREFERRED EMBODIMENTS

The following examples illustrate the various aspects of the invention in greater detail. However, it should be recognized that they are only illustrative. Variations from what is disclosed will undoubtedly occur to those skilled in the art, but will nevertheless be embraced by the inventive concept of the invention. All parts, unless otherwise indicated, are by weight.

EXAMPLE 1

An adipic acid waste stream containing molten dibasic acid was heated at 140° C. with about 2.0% of sulfuric acid while methanol is introduced. Some of the acid was consumed in the process by reaction with ammonia which is present in the waste stream by hydrolysis of nitriles. Vapors of methanol, water and small quantities of methyl esters were removed and condensed.

With temperature being maintained at about 140° C., esterification continued. The pH of the reaction mixture was tested with a glass electrode calibrated in water. The pH reading remained negative. Esterification was deemed complete when the waste stream achieved an acid number of 5. The total esterification process took about three hours.

At the conclusion of the esterification a precipitate containing a high percentage of copper and vanadium was optionally filtered off. About 2.0% Ca(OH)$_2$ was added to the waste stream containing the methyl esters and the mixture held at 135° C. for two hours. The mother liquor was then distilled to remove dibasic acid methyl esters.

EXAMPLE 2

A sample of adipic acid waste stream containing 200 lbs. of dibasic acid was loaded into a 50 gallon stainless steel pot. The sample was then esterified with methanol using a H$_2$SO$_4$ catalyst at 2.0%. The esterification was controlled by a glass electrode at a pH of less than 0. The esterification was stopped when the sample reached an acid number of 4.8 and the batch filtered to remove about 11 lbs. of wet filter cake.

The sample was then neutralized with excess Ca(OH)$_2$ and vacuum distilled to remove 160 lbs. of dibasic acid methyl ester.

EXAMPLE 3

An adipic acid waste stream containing about 33% DBA and 1000 ppm copper was charged with sulfuric acid (1.0% by wt.), and dehydrated at 140° C./1 atm. until the moisture content was 4.9%. Methanol was then charged below the surface of DBA at 140° C., while water-rich methanol was flashed off. The esterification process was continued until the acid number of crude product was about 10 (3 hours).

The crude esters (377 g.) were then charged with 6.3 g. sodium carbonate. After removal of a small forecut (3.5% by wt.) at 130° C., the esters were distilled at 113-123° C./25 mm. Hg. Refined ester having an acid number of 0.34 and an alkaline color of 1-3 was obtained in 91.6% yield. The residue from the distillation was easily removed from the reaction flask by the addition of water at 90°-100° C.

EXAMPLE 4

An adipic acid waste stream containing about 33% DBA and 1000 ppm copper was dehydrated at 140° C./300 mm. Hg until the moisture content was 1.4%. Methanol was then charged below the surface of DBA at 140° C. in the presence of H$_2$SO$_4$ (1%), while water-rich methanol was flashed off. The esterification process was continued until the acid number was 7.7.

The crude esters (397 g.) were then charged with 4.9 g. sodium carbonate. After removal of a small forecut (2.5% by wt.) at 130° C., the esters were distilled at 108°-125° C./25 mm. Hg. Refined ester having acid number of 0.52 and an alkaline color of 1-5 was obtained in 91.6% yield. The residue from the distillation was easily removed by the addition of hot water.

EXAMPLE 5

The preparation of dibasic esters from a waste stream in the manufacture of dodecanedioic acid is set forth below. Parts are by weight.

One part of the waste stream containing approximately 0.667 part of dibasic acids, 0.225 part of water, 0.004 part monobasic acids, 0.001 part of nitric acid and 0.103 part of nitro acids and trace amounts of metals, e.g. copper, is heated to 260° C. and maintained at that temperature for one hour during which time substantially all of the water evaporates. The resultant product is cooled and esterified at 140° C. by vigorous contact with 0.775 part of methanol in the presence of 0.46 part of a 50% aqueous solution of sulfuric acid. Approximately one part of the crude esterified product which contains 0.023 part of sulfate (as ammonium compounds) and 0.02 part of dissolved methanol is contacted with 0.0155 part of calcium hydroxide, then heated to 160° C. and maintained at that temperature for two hours following which the resultant material is distilled at 195° C. and 5 mm. Hg abs. to yield 0.9 part of purified dimethyl ester product which has an alkaline color of less than 4 and an acid number less than about 1.

UTILITY

This invention enables one to recover valuable dibasic acid methyl esters from a waste stream containing dibasic acids. These methyl esters are free from various contaminants which would detrimentally affect the end uses to which the methyl esters would be put. Formerly such waste streams were burned thereby adding to ecological pollution. The advantages of reusing instead of burning are obvious.

The uncontaminated methyl esters of dibasic acids may be used as solvents for acrylic lacquers, solvents for industrial finishes, and as intermediates for plasticizers, film forming vehicles and strip-coatings for steel and aluminum. The methyl esters can also be used in automotive topcoats and undercoats. The elimination of colored materials from the esters permit their use as solvents and as intermediates for plasticizers. Prior esters were variable and dark in color particularly when subjected to alkaline conditions during and after esterification. These contaminants altered the color of topcoat finishes. This problem is easily resolved by using the methyl esters derived from the process of this invention.

I claim:

1. A process for making alkyl esters of dibasic saturated acids having 4 through 12 carbons from a liquor containing said acids which comprises
  a. heating said liquor to a temperature of about 130° to 150° C to substantially remove water, oxides of nitrogen and nitric acid;
  b. esterifying said acids at a temperature of about 120° to 160° C with an alcohol having 1 through 4 carbons in the presence of an acid catalyst while substantially removing all of the water formed and thereby producing an esterified product; and
  c. distilling off volatile nitrogen-containing compounds, esters of monobasic acids, and the alkyl esters of dibasic acid, in succession, from the esterified product, in the presence of excess dry base selected from the group consisting of Na$_2$CO$_3$, NaHCO$_3$, Ca(OH)$_2$, CaO and K$_2$CO$_3$.

2. The process of claim 1 wherein the liquor in step (a) is heated further prior to step (b) at a temperature of no more than about 270° C for a time sufficient to reduce the volatility of heat-discoloring compounds therein.

3. The process of claim 1 wherein the product of step (b) is heated further prior to step (c) at a temperature of no more than about 270° C for a time sufficient to reduce the volatility of heat-discoloring compounds therein.

4. The process of claim 1 wherein in step (b) the alcohol is methanol and the catalyst is H$_2$SO$_4$ and in step (c) the dry base is selected from the group consisting of Na$_2$CO$_3$, at a level of at least about 0.7 per one equivalent of titratable acidity, and Ca(OH)$_2$.

5. The process of claim 1 wherein NH$_3$ is removed in step (c) by distillation at about 180° C for about 30 minutes.

6. The process of claim 5 wherein the esters of monobasic acids are substantially removed in a forecut.

7. The process of claim 1 wherein the esters of monobasic acids are substantially removed in a forecut.

* * * * *